United States Patent [19]
Krause et al.

[11] Patent Number: 5,672,335
[45] Date of Patent: Sep. 30, 1997

[54] USE OF METAL COMPLEXES AS LIVER AND GALLBLADDER X-RAY DIAGNOSTIC AGENTS

[75] Inventors: Werner Krause; Thomas Balzer; Wolf-Rüdiger Press; Gabriele Schuhmann-Giampieri; Ulrich Speck, all of Berlin; Andreas Mühler, Neuenhagen, all of Germany

[73] Assignee: Schering Aktiengesellschaft, Berlin, Germany

[21] Appl. No.: 487,094

[22] Filed: Jun. 6, 1995

Related U.S. Application Data

[63] Continuation-in-part of Ser. No. 387,408, Feb. 13, 1995, which is a continuation-in-part of Ser. No. 351,086, Nov. 30, 1994, abandoned.

[51] Int. Cl.$^6$ ................................................ A61B 5/055
[52] U.S. Cl. ............... 424/9.42; 424/9.364; 424/9.365; 534/16; 556/50; 556/55; 556/63; 556/77; 556/105; 556/116; 556/134; 556/148; 436/173; 514/492; 514/502; 514/836
[58] Field of Search ............... 424/9.42, 9.365, 424/9.364; 534/16; 556/50, 55, 63, 77, 105, 116, 134, 148; 128/653.4, 654; 436/173; 514/492, 502, 836

[56] References Cited

U.S. PATENT DOCUMENTS

| | | | |
|---|---|---|---|
| 4,647,447 | 3/1987 | Gries et al. | 424/9.36 |
| 4,880,008 | 11/1989 | Lauffer | 128/654 |
| 4,899,755 | 2/1990 | Lauffer et al. | 128/654 |
| 5,250,285 | 10/1993 | Lauffer et al. | 424/9 |
| 5,316,756 | 5/1994 | Gries et al. | 424/9.365 |
| 5,318,771 | 6/1994 | Lauffer et al. | 424/9 |
| 5,399,340 | 3/1995 | Radüchel et al. | 424/9 |
| 5,482,700 | 1/1996 | Deutsch et al. | 424/9.364 |

FOREIGN PATENT DOCUMENTS

| | | |
|---|---|---|
| 0 230 893 | 3/1987 | European Pat. Off. . |
| 0 405 704 | 1/1991 | European Pat. Off. . |
| 94/27644 | 12/1994 | WIPO . |
| 95/15319 | 6/1995 | WIPO . |

*Primary Examiner*—Gary E. Hollinden, Ph.D
*Attorney, Agent, or Firm*—Millen, White, Zelano, & Branigan, P.C.

[57] ABSTRACT

Metal complexes containing a metal of atomic numbers 39–42, 44–51 or 56–83 and a complexing agent can be used for the production of contrast media for use in the contrast-enhanced computer tomography of the liver and the biliary tracts.

35 Claims, No Drawings

USE OF METAL COMPLEXES AS LIVER AND GALLBLADDER X-RAY DIAGNOSTIC AGENTS

CROSS-REFERENCE TO RELATED APPLICATION

This application is a continuation-in-part of U.S. Ser. No. 08/387,408, filed Feb. 13, 1995, which, in turn, is a continuation-in-part of U.S. Ser. No. 08/351,086, filed Nov. 30, 1994, now abandoned. Both Ser. Nos. 08/387,408 and 08/351,086 are hereby incorporated by reference in their entirety.

SUMMARY OF THE INVENTION

The invention relates to the use of metal complexes in liver and gallbladder X-ray diagnosis by conventional polychromatic X-ray radiation.

The early detection of focal liver diseases, especially liver metastases and liver tumors, is one of the most important diagnostic problems in oncology. Four imaging processes are available for this purpose: scintigraphy, ultrasonography, computer tomography and magnetic resonance imaging (MRI). Each of the processes has specific advantages and disadvantages. None is considered optimal by itself according to the present state of the art, and practically every process would benefit by the presence of more specific, compatible contrast media that can be administered intravenously [Hamed, R. K.; Chezmar, J. L.; Nelson, R. C.: Imaging of patients with potentially resectable hepatic neoplasms. AJR 159, 1191–1194 (1992)].

Scintigraphy offers too little spatial resolution and is limited in it use by the insufficient or too high (usable only for a few types of tumors) specificity of the radiopharmaceuticals, so that it is not discussed in the above-mentioned survey article. At this time, sonography is also not a sufficiently reliable technique to detect solid focal liver changes, since the latter often are not sufficiently distinguished from the healthy liver tissue in their acoustical properties. Only during the operation, after exposing the liver and with the use of high-frequency transducers, can smaller lesions in the liver tissue be detected. Magnetic resonance imaging is able to detect the entire liver with good spatial resolution and depending on the mode of measurement also with good tissue differentiation. For MRI, well-tolerated, effective contrast media that can be administered intravenously and which further improve the use of this imaging process are in clinical testing. But drawbacks are artifacts of movements in the highly-resolving measuring processes taking several minutes and the high costs of the devices themselves, which limit their availability.

Computer tomography (CT) is actually the ideal technique for liver diagnosis. With modern devices, the entire liver can be detected with excellent spatial resolution within about 30 seconds. An individual liver layer requires about 1 second, so that movements by breathing and peristalsis play hardly any role. The costs of CT are clearly lower than those of MRI. But the drawback of the low tissue density resolution must be compensated for by contrast media. With the now clinically available contrast media, there are the following possibilities:

1. The contrast media are intravenously injected or infused quickly and at a high dose (50–200 g). For a few minutes, a difference in contrast between the lesion and the normal liver tissue occurs, which is based on differences in the perfusion, the relative blood volume of the tissues and the extracellular space. Only with the mentioned modern, very quick CT can this period of unequal distribution of the contrast media be used for diagnosis. Nevertheless, e.g., 20–30% of the liver metastases are not found.

2. 4–6 hours after administration of at least 120 g of the usual urographic contrast media, an improved contrast between the contrast medium-absorbing healthy liver parenchyma and the, in most cases, non-absorbing focal liver lesions is observed in some of the patients. But this technique designated as delayed scanning is not sufficiently reliable and informative, so that it is not used routinely.

3. In the arterial hepatography, a catheter has to be inserted, e.g., in the A. mesenterica, the patient is then brought to the CT device and the scan is performed during the infusion of about 150 ml of contrast medium. This technique is invasive, time-consuming and expensive, but at this time produces the most reliable information on the existence and location of liver metastases. This invention is of decisive importance for the decision on the resectability of metastases. The CT with arterial hepatography is therefore regularly performed pre-operatively despite the expense.

The above-described problems are the result of the fact that the now available X-ray contrast media as such are urographic products, which do not accumulate in the liver. To produce some contrast nevertheless, the liver is inundated for a short time with very large amounts of contrast medium through the blood stream ("dynamic scanning") or 1–2% of the contrast medium is used, which is found later on in the liver parenchyma of some of the patients ("delayed scan").

It can easily be seen that a demand for an improved diagnosis of focal liver lesions exists, since the existing processes are too poorly efficient, too expensive or too stressful for the patients. Therefore, innumerable attempts have been made over the decades to develop liver-specific X-ray contrast media that can be administered intravenously. See, e.g., the following tables.

| Title | Company | Examiner | Status |
|---|---|---|---|
| Oil Emulsions i.v. | | | |
| AG 60-99 | Guerbet | Lamarque | 100 patients, terminated |
| EOE 13 | — | Verness | several hundred patients, terminated |
| EOE 14 | Abbott | — | Only preclinic |
| Perfluorooctyl bromide | Boehringer Ingelheim | Bruneton | Clinical testing terminated |
| intraiodol | — | Lunderquist | Clinical testing terminated |
| Oil Emulsions i.a. | | | |
| Lipiodol | — | Numerous users | Without approval |
| Liposomes | | | |
| Amidotrizoate or iotrolan | — | Seltzer | Animal experiments |
| Iopromide | Schering | Felsenburg/ Böhle | Animal experiments |
| Iopamidol | Bracco | Musu | Animal experiments |
| Ioxaglat | Guerbet | Corot | Animal experiments |

From the large number of preparations tested, only a few will be mentioned. Thorotrast (colloidal suspension of thorium oxide) produced excellent liver contrast, but was not excreted. The α-radiator thorium caused liver tumors decades after the administration. In 1940, Schering A. G. marketed the preparation Hepatoselectan, an emulsion of very fine droplets of a triiodinated oil. Because of acute side effects, it had to be taken off the market. Subsequent products of other companies and research groups (EOE-13, AG-60-99, etc.) were already given up during the clinical tests because of the same problems.

In addition to a multitude of pharmaceutical problems, all particular preparations (suspensions, emulsions, liposomes) have the drawback of causing characteristic difficult-to-avoid side effects in the high dosage (5–20 g) for X-ray diagnosis. In the 1970's and early 1980's, therefore, great efforts were made to find water-soluble X-ray contrast media, which accumulate in the liver—sufficiently for the CT. Such substances were provided with up to 6 iodine atoms per molecule and last but not least, therefore, were in some cases very effective and well-tolerated in the animal-experiment test. Noticeably, there were great differences in the effectiveness in the individual animal species. But until now, none of the examined iodine-containing water-soluble contrast media has reached a sufficient concentration in the liver in humans, which would make a development for the CT appear promising. A characteristic example for the many abortive attempts was published by Mützel, W.; Wegener, O. H.; Souchon, R. and Weinmann, H. -J. Water-soluble contrast agents for computed tomography of the liver: experimental studies in dog. In Amiel (edt.): Contrast media in radiology, Lyon 1981, Springer Verlag Berlin Heidelberg New York 1982, pp. 320–323, Table 1. Also in this case, insufficient liver contrast was found in humans in contrast to many animal species.

Intravenous cholegraphic agents, such as Iotroxinate, Iodoxamate and Ioglycamate accumulate selectively in the liver. But this process is very limited in capacity. At a concentration corresponding to 5 µg of iodine/ml in the plasma, about a 5-fold concentration (25 µg of iodine/ml) in the liver is achieved. At a concentration corresponding to 50 µg of iodine/ml in the plasma, hardly a 2-fold concentration is achieved in the liver. At 500 µg of iodine/ml in the plasma, the concentration in the liver is clearly lower than in the plasma and therefore largely worthless diagnostically. Thus, at this concentration, a differentiation of actively accumulating tissues and simple perfusion is impossible. Since computer tomography first detects iodine concentrations starting from about 1 mg/ml (1000 µg/ml) with sufficient reliability, selective accumulation of these agents is not diagnostically useful (Speck, U.; Mützel, W.; Herz-Hübner, U.; Siefert, H. M. Pharmakologie Iotroxinsäure eines neuen intravenösen Cholegraphicums I. [Pharmacology of Iotroxinic Acid of a New Intravenous Cholegraphic Agent I.] Pharmakokinetik und Radiologie beim Tier [Pharmacokinetics and Radiology in Animals]. Drug Res. 28, 2143–2149 (1978).

Thus, it remains to be noted that a demand exists for specific X-ray contrast media that are preferably water-soluble and therefore pharmaceutically well-characterizable, stable, compatible and effective in not too high a dose, because, despite decades of efforts, no single product is available on the market or in a promising stage of clinical testing. Because of the unpredictable species dependence on intake, concentrating and excreting through the liver by animal-experiment tests, such preparations can be discovered only with difficulty; also, after many disappointing results in humans, animal-experimental findings are no longer considered as an indication for suitability or non-suitability of a substance or class of substances.

Metal-containing contrast media for the magnetic resonance imaging also absorb X-rays. It was therefore attempted in individual cases to use these substances for computer tomography (Schild, H. H. et al.: Gadolinium DTPA (Magnevist®) as contrast medium for the arterial DSA. Fortschr. Röntgenstr. [Advances in X-ray Radiation] 160, 218–221 (1994); Quin, A. D. et al.: Gd-DTPA: An alternative contrast medium for CT. J. Comput. Assist. Tomogr. 18, 634–636 (1994)). It is to be taken into consideration that the previously available metal complexes bind only to one opacifying metal ion per molecule, while the iodinated X-ray contrast media contain 3 or 6 iodine atoms per molecule. Despite greater effectiveness of several metal ions relative to iodine (Zwicker, C.; Langer, M.; Langer, R., Keske, U. Comparison of iodinated and noniodinated contrast media in computed tomography. Invest. Radiol. 26, 162–164 (1991)), the iodinated contrast media thus far cannot be replaced by metal chelates in any relevant indication.

A drawback of metal chelates is the significantly lower content of an X-ray radiation-absorbing element in the molecules (iodinated X-ray contrast media: 3 or 6 iodine atoms/molecule; MRI contrast media: 1 metal ion/molecule). The opacification is correspondingly weak, so that the metal complexes were used almost only for experimental studies with X-rays. In MRI, such low concentrations of metal ions are sufficient, since, in MRI, the metal ions are not visualized as in the case of X-ray imaging. Instead, in MRI, the metal ions quasi-catalytically influence the protons thereby producing contrast within the image.

An object of the invention, therefore, is to provide pharmaceutical substances, which are suitable as contrast media for X-ray diagnosis, especially computer tomography, of the liver and biliary tracts.

Upon further study of the specification and appended claims, further objects and advantages of this invention will become apparent to those skilled in the art.

These objects are achieved by this invention.

It has been found that metal complexes of elements of atomic numbers 39–42, 44–51 or 56–83 and complexing agents, are suitable for the production of contrast media for use in the contrast-enhanced computer tomography of the liver and of the biliary tracts.

It was surprising that with certain groups of metal chelates, despite clearly worse preconditions on the part of the radiation-absorbing action per molecule in comparison to iodinated agents, an absorption of the X-rays in the liver, completely satisfactory for computer tomography, was achieved for the first time in humans, without the use of approximately as high dosages as is the case in the unspecific iodinated X-ray contrast media. Simultaneously, it was shown that the concentration in the liver takes place quickly and is sustained long enough for the computer-tomographic diagnosis process. The administration can take place intravenously. The compatibility is very good in the required dose range.

In general, metal chelate complexes with a molecular weight under 1500 daltons (D), which contain at least one metal ion of atomic number 39–42, 44–51 or 56–83 capable of X-ray absorption, are suitable. Preferred are those chelate complexes that are characterized by two carboxyl groups not involved in the complexing of the opacifying element. The substances contain in the molecule at least one structural element having at least three C atoms, which is more lipophilic than gadolinium-DTPA or the entire lipophilic (distribution coefficient of butanol/tris-buffer pH 7.6>0.0002) of the molecule is higher than that of the gadolinium-DTPA. The molecule also contains one or more metal ions of atomic numbers 39–42, 44–51 and 56–83 in a firm complex-bound way, and the binding constant or stability constant preferably exceeds $10^{14}$. Such substances and their production are described, i.a., in EP 0 405 704; EP 0 230 893; U.S. Pat. No. 4,880,008; U.S. Pat. No. 4,899,755; U.S. Pat. No. 5,250,285 and U.S. Pat. No. 5,318,771.

Preferred substances according to the invention are described by general formulas I to XI:

Formula I

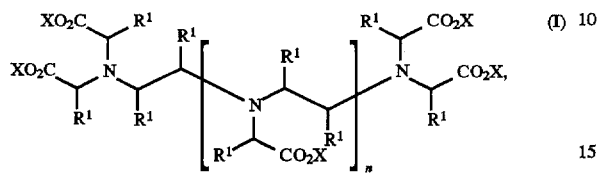 (I)

wherein

X, independently of one another, stand for a hydrogen atom, or for a metal ion equivalent of an element of atomic numbers 39–42, 44–51 or 56–83, n stands for the numbers 0, 1 or 2, and $R^1$, independently of one another, stand for a hydrogen atom or a radical of formula Ia

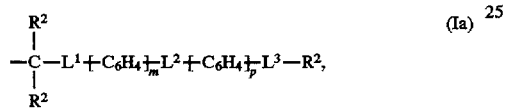 (Ia)

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another and in which free carboxyl groups not used for complexing in each case can also be present as salts of physiologically compatible cations or as an amide of formula

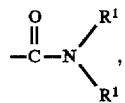

wherein $R^1$ has the above-indicated meaning,

Formula II

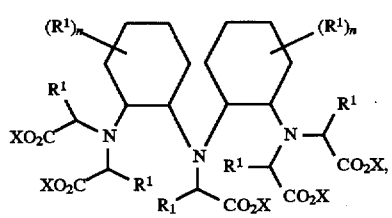 (II)

wherein

X, independently of one another, stand for a hydrogen atom or for a metal ion equivalent of an element of atomic numbers 39–42, 44–51 or 56–83, n stands for the numbers 0, 1 or 2, and $R^1$, independently of one another, stand for a hydrogen atom or a radical of formula IIa,

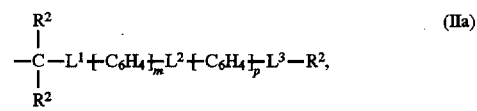 (IIa)

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are connected directly with one another, in which the six-membered carbon rings present in formula II can also be aromatic, and in which free carboxyl groups not used for complexing in each case can also be present as salts of physiologically compatible cations or as an amide of formula

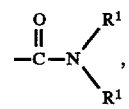

in which $R^1$ has the above-indicated meaning,

Formula III

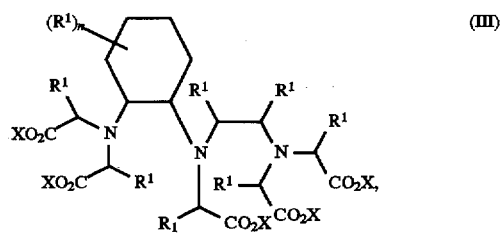 (III)

wherein

X, independently of one another, stand for a hydrogen atom or for a metal ion equivalent of an element of atomic numbers 39–42, 44–51 or 56–83, n stands for the numbers 0, 1 or 2, and, $R^1$, independently of one another, stand for a hydrogen atom or a radical of formula IIIa

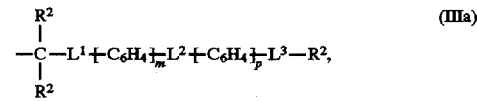 (IIIa)

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are connected directly with one another, in which the six-membered carbon ring present in formula III can also be aromatic, and in which free carboxyl groups not used for complexing in each case also can be present as salts of physiologically compatible cations or as an amide of formula

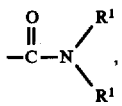

wherein $R^1$ has the above-indicated meaning,

Formula IV

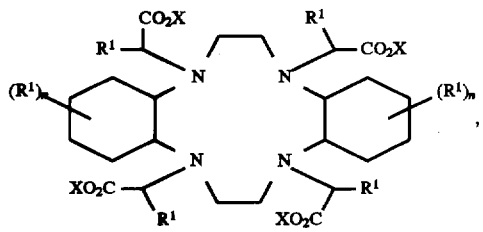

(IV)

wherein

X, independently of one another, stand for a hydrogen atom or for a metal ion equivalent of an element of atomic numbers 39–42, 44–51 or 56–83, n stands for the numbers 0, 1 or 2, and $R^1$, independently of one another, stand for a hydrogen atom or a radical of formula IVa

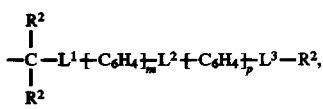

(IVa)

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another, in which the six-membered carbon rings present in formula IV can also be aromatic, and, in which free carboxyl groups not used for complexing can in each case also be present as salts of physiologically compatible cations or as an amide of formula

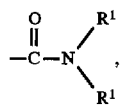

wherein $R_1$ has the above-indicated meaning,

Formula V

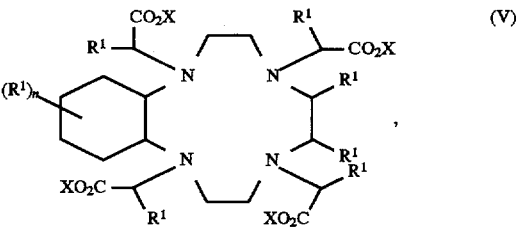

(V)

wherein

X, independently of one another, stand for a hydrogen atom or for a metal ion equivalent of an element of atomic numbers 39–42, 44–51 or 56–83, n stands for the numbers 0, 1 or 2, and $R^1$, independently of one another, stand for a hydrogen atom or a radical of formula Va

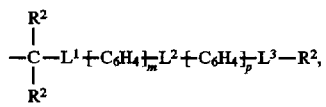

(Va)

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another, in which the six-membered carbon ring present in formula V can also be aromatic, and in which free carboxyl groups not used for complexing can in each case also be present as salts of physiologically compatible cations or as an amide of formula

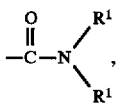

wherein $R^1$ has the above-indicated meaning,

Formula VI

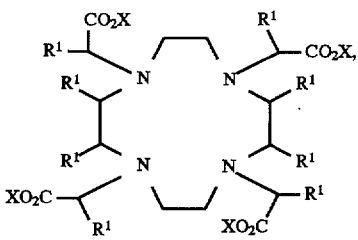

wherein

X, independently of one another, stand for a hydrogen atom, or for a metal ion equivalent of an element of atomic numbers 39–42, 44–51 or 56–83, n stands for the numbers 0, 1 or 2, and $R^1$, independently of one another, stand for a hydrogen atom or a radical of formula VIa

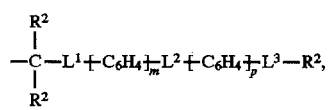

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another and in which free carboxyl groups not used for complexing can in each case also be present as salts of physiologically compatible cations or as an amide of formula

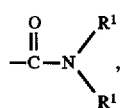

wherein $R^1$ has the above-indicated meaning,

Formula VII

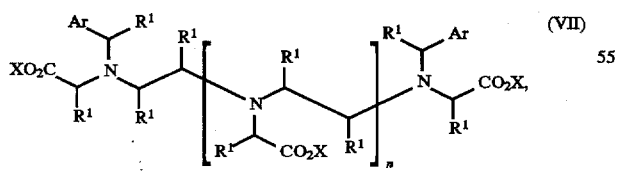

wherein

X, independently of one another, stand for a hydrogen atom, or for a metal ion equivalent of an element of atomic numbers 39–42, 44–51 or 56–83, n stands for the numbers 0, 1 or 2, and $R^1$, independently of one another, stand for a hydrogen atom or a radical of formula VIIa

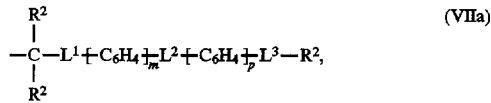

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— or a $C_1$–$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another and in which free carboxyl groups not used for complexing can in each case also be present as salts of physiologically compatible cations or as an amide of formula

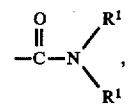

wherein $R^1$ has the above-indicated meaning, and

Ar, independently of one another, stand for a saturated or unsaturated, optionally bicyclic, $C_5$–$C_{10}$ ring, which optionally is interrupted by one to two oxygen, sulfur and/or nitrogen atoms, and optionally is substituted by one to three phenyl, pyridyl, HO, HS, HOOC, $R^1$OOC, $R^1$O, $R^1$NHOC, $R^1$CONH, $R^1$ and/or $H_2$N groups, which further optionally contains one to three carbonyl, thiocarbonyl and/or imino groups.

Formula VIII

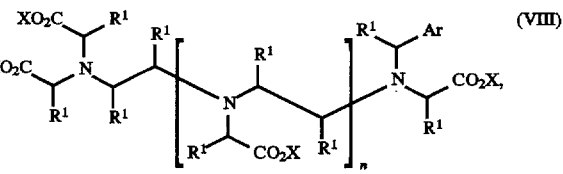

wherein

X, independently of one another, stand for a hydrogen atom, or for a metal ion equivalent of an element of atomic numbers 39–42, 44–51 or 56–83, n stands for the numbers 0, 1 or 2, and $R^1$, independently of one another, stand for a hydrogen atom or a radical of formula VIIa

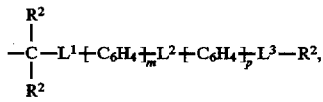

wherein m and p, in each case independently, stand for the numbers 0 or 1, $R^2$, independently of one another, stand for a hydrogen atom or a branched or unbranched, saturated or unsaturated $C_1$–$C_6$ aliphatic radical, and $L^1$, $L^2$ and $L^3$, in each case independently, stand for a direct bond, an oxygen atom, a sulfur atom, —N(H)—, —N($R^2$)— group or a $C_1$-$C_{10}$ alkylene chain, which optionally is interrupted by an oxygen or a sulfur atom, an —N(H)— or an —N($R^2$)— group, in which if m and/or p is equal to zero, no two or more heteroatoms are directly connected with one another and in which free carboxyl groups not used for complexing can in each case also be present as salts of physiologically compatible cations or as an amide of formula $$\underset{\diagdown R^1}{\overset{O}{\underset{\|}{-C}}-N\diagup R^1}$$

wherein $R^1$ has the above-indicated meaning, and

Ar, independently of one another, stand for a saturated or unsaturated, optionally bicyclic, $C_5$-$C_{10}$ ring, which optionally is interrupted by one to two oxygen, sulfur and/or nitrogen atoms, and optionally is substituted by one to three phenyl, pyridyl, HO, HS, HOOC, $R^1$OOC, $R^1$O, $R^1$NHOC, $R^1$CONH, $R^1$ and/or $H_2N$ groups, which further optionally contains one to three carbonyl, thiocarbonyl and/or imino groups.

Formula IX (IX)

wherein

X, independently of one another, stand for a hydrogen atom, or for a metal ion equivalent of an element of atomic numbers 39–42, 44–51 or 56–83, y stands for the number zero or one and $R^3$ stands for a $C_1$-$C_5$ alkyl radical or a benzyl radical, in which free carboxyl groups not used for complexing can in each case also be present as salts of physiologically compatible cations or as an amide of formula $$\underset{\diagdown R^1}{\overset{O}{\underset{\|}{-C}}-N\diagup R^1}$$

wherein $R^1$ has the above-indicated meaning,

Formula X (X)

wherein

X, independently of one another, stands for a hydrogen atom, or for a metal ion equivalent of an element of atomic numbers 39–42, 44–51 or 56–83, $R^3$ stands for a methyl, ethyl, n-propyl, n-butyl or a benzyl radical, in which free carboxyl groups not used for complexing can in each case also be present as salts of physiologically compatible cations or as an amide of formula $$\underset{\diagdown R^1}{\overset{O}{\underset{\|}{-C}}-N\diagup R^1}$$

wherein $R^1$ has the above-indicated meaning,

Formula XI (XI)

wherein

X, independently of one another, stand for a hydrogen atom, or for a metal ion equivalent of an element of atomic numbers 39–42, 44–51 or 56–83, $R^3$ stands for a methyl, ethyl, n-propyl, n-butyl or a benzyl radical, in which free carboxyl groups not used for complexing can in each case also be present as salts of physiologically compatible cations or as an amide of formula $$\underset{\diagdown R^1}{\overset{O}{\underset{\|}{-C}}-N\diagup R^1}$$

wherein $R^1$ has the above-indicated meaning.

The symbol stands for a $C_6$-ring, which can be saturated, unsaturated or aromatic, and which is substituted n-fold by group $R^1$.

As radicals of general formulas Ia, IIa, IIIa, IVa, Va, VIa, VIIa and VIIIa, there can be mentioned as examples: benzyl ($-CH_2-C_6H_5$), methoxybenzyl ($-CH_2-C_6H_4-O-CH_3$), ethoxybenzyl ($-CH_2-C_6H_4-O-CH_2CH_3$), propoxybenzyl ($-CH_2-C_6H_4-O-C_3H_7$), butoxybenzyl ($-CH_2-C_6H_4-O-C_4H_9$), pentoxybenzyl ($-CH_2-C_6H_4-O-C_5H_{11}$), benzyloxybenzyl ($-CH_2-C_6H_4-O-CH_2-C_6H_5$), methylbenzyl ($-CH_2-C_6H_4-CH_3$), ethylbenzyl ($-CH_2-C_6H_4-CH_2CH_3$), propylbenzyl ($-CH_2-C_6H_4-C_3H_7$), butylbenzyl ($-CH_2-C_6H_4-C_4H_9$), pentylbenzyl ($-CH_2-C_6H_4-C_5H_{11}$) and benzylbenzyl ($-CH_2-C_6H_4-CH_2-C_6H_5$) radicals. Preferably, the compounds of formulas I–VIII contain, respectively, 1–2 radicals of formulas Ia–VIIIa.

Of the metal ions, the lanthanides are preferred, e.g., ions of Gd, Dy, Ho, Er, Yb and Lu, preferably Yb or Lu. In measurements under practical conditions (see Example 1), holmium, erbium and ytterbium have proven better-suited than the elements gadolinium and dysprosium generally preferred for MRI. Thulium appears less suitable under economic aspects because of the high price, but it is in principle also suitable. But, other elements can also be used such as elements of atomic numbers 72–83, for example, Bi or Pb, elements of atomic numbers 39–42 and elements of atomic numbers 44–51. In general, every increase of effect is very desirable, since simultaneously the dosage is reduced and thus the compatibility is improved and the costs are lowered.

As physiologically compatible cations, there can be mentioned as examples sodium$^+$, calcium$^{2+}$, magnesium$^{2+}$ and zinc$^{2+}$, as well as organic cations such as meglumine, glucosamine, arginine, ornithine, lysine and ethanolamine.

The mentioned metal complexes are preferably used in the form of their sterile, aqueous solutions. In addition to the metal complexes absorbing the X-rays, the aqueous solution can contain the usual pharmaceutical adjuvants, such as buffers, bases, acids, stabilizers, solubilizers, substances for matching the osmolality and viscosity, pharmacologically effective additives and an excess of free complexing agents or their salts/complexes with weakly bound physiologically compatible ions, such as calcium$^{2+}$, magnesium$^{2+}$ or zinc$^{2+}$ to, for example, improve the elimination of heavy metal ions. Suitable such substances and their ranges of concentration are known to one skilled in the art or can be gathered from the literature.

The metal complexes are used preferably in a concentration of about 0.1 mol–1.0 mol of opacifying metal ion. Higher or lower concentrations are possible depending on the requirements and the solubility of the compound in question. The dosage for the contrast-enhancement in the liver is preferably about 0.1–1.5 mmol/kg of body weight, especially 0.2–0.6 mmol/kg.

The administration can take place in the ways usually employed in medicine. Preferably, the agents are administered by intravenous infusion or injection over a period of about 1 minute to 30 minutes.

In summary, it is to be noted that it has been possible for the first time with the family of substances described herein to achieve a specific contrast medium concentration in the liver in humans, which results in useful diagnostic information with the now available computertomographic technology. This finding is all the more surprising as ♦ preparations for this purpose have been sought in vain for decades, ♦ iodinated X-ray contrast media did not satisfy the requirements despite the presence of all molecular properties theoretically to be required and a substantially higher content of opacifying element in the molecule, ♦ the action of the substances according to the invention when used in magnetic resonance imaging occurs at concentrations lower by a factor of 10 than required for X-ray computer tomography; and such lower concentrations are achieved by a great many X-ray contrast media in the liver of humans, without these X-ray contrast media being able to be used for computer tomography, MRI or another opacifying process to improve diagnosis of focal liver changes, ♦ findings from animal experiments with respect to suitability of contrast media for contrast enhancement in liver computer tomography thus far have proven completely unreliable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1

(a) 3,6,9-Triaza-3,6,9-tris(tert-butoxycarbonylmethyl)-4-(4-ethoxybenzyl)undecanedioic AcidDi-tert-butyl Diester At 0° C., 5.85 g (7.5 mmol) of 3,6,9-triaza-3,6,9-tris(tert-butoxycarbonylmethyl)-4-(4-hydroxybenzyl)undecanedioic acid di-tert-butyl diester (Example 9f of DOS 37 10 730) is combined in 100 ml of tetrahydrofuran with 0.30 g (10 mmol) of 80% strength sodium hydride. To this mixture is added 1.56 g (10 mmol) of iodoethane and the mixture is stirred for 3 hours. Then the solution is combined with water, tetrahydrofuran is distilled off, and the aqueous emulsion is extracted with diethyl ether. The crude product obtained after drying over sodium sulfate and concentration of the solvent is chromatographed on silica gel (system: hexane/ether/triethylamine 70:30:5).

(b) 3,6,9-Triaza-3,6,9-tris(carboxymethyl)-4-(4-ethoxybenzyl)undecanedioic Acid 3.64 g (4.5 mmol) of the tert-butyl ester disclosed in Example 1(a) is dissolved in 25 ml of trifluoroacetic acid, stirred for one hour at room temperature. The solution is then combined with diethyl ether, the precipitate is suctioned off, washed with ether and dried at 40° C. under vacuum over phosphorus pentoxide. The crude product is dissolved in water and combined under agitation with active carbon. The mixture is filtered off from the carbon and lyophilized three times to remove residual trifluoroacetic acid.

(c) Disodium Salt of the Gadolinium Complex of 3,6,9-Triaza-3,6,9-tris(carboxymethyl)-4-(4-ethoxybenzyl)undecanedioic Acid 528 ml (1 mmol) of the complex-forming acid described in the preceding example is dissolved in 40 ml of water and complexed at 80° C. with 181 mg (0.5 mmol) of $Gd_2O_3$. Then the mixture is neutralized with 2 ml of 1N NaOH, stirred with activated carbon, filtered, and the filtrate is freeze-dried.

Analogously, the corresponding lutetium complex is obtained with lutetium oxide, $Lu_2O_3$, and the corresponding ytterbium complex is obtained with ytterbium oxide, $Yb_2O_3$.

Example 2

The following table lists, in Houndsfield units (HU), density enhancement of the healthy liver parenchyma 10 and 60 minutes after infusion of a 0.25 molar solution of the gadolinium(III) complex of 3,6,9-triaza-3,6,9-tris (carboxymethyl)-4-(4-ethoxybenzyl)-undecanoic acid disodium salt in 5 patients with liver metastases at a dose of 0.35 mmol/kg. This dose corresponds to about 16 g of the complex per 70 kg of patient.

TABLE 1

|  | 10 min p. inf./HU | 60 min p. inf./HU |
|---|---|---|
| Patient 1 | 19 | 26 |
| Patient 2 | 12 | 25 |
| Patient 3 | 10 | 17 |
| Patient 4 | 18 | 32 |
| Patient 5 | 15 | 32 |

In comparison, according to Mützel et al., 1982, the hexaiodinated SH L 433 (shown below), developed specially for the liver diagnosis, in a dose corresponding to 360 mg of iodine/kg (about 25 g of iodine per 70 kg of patient), caused an enhancement of only <10 HU (monkey, dog, mouse: >40HU). Iotroxinate (hexaiodinated, 2 carboxyl groups), excreted in a biliary manner in humans to about 90%, reaches only 15 HU in the liver in the maximum compatible dose corresponding to about 7 g of iodine/70 kg of patient (Hübner, K. H.: Computertomographische Densitometrie von Leber, Milz und Nieren bei intravenös verabreichten lebergängigen Kontrastmitteln in Bolusform. [Computer Tomographic Densitometry of Liver, Spleen and Kidneys in Intravenously Administered Contrast Media that Pass Through the Liver in Bolus Form.] Fortschr. Röntgenstr. 129, 289–297 (1978)).

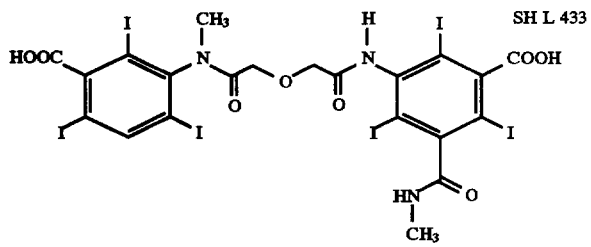

SH L 433

In comparison, a many times higher X-ray absorption in the liver of humans is achieved with about 3.5 g of gadolinium in the form of a complex, which contains only one gadolinium ion/molecule, than with 25 g of iodine of SH L 433 or 7 g of iodine of the Iotroxinate, although the latter two X-ray contrast media are hexaiodinated compounds.

Example 3

The following solution is produced:

0.1 molar of the holmium(III) complex of the 3,6,9-triaza-3,6,9-tris(carboxymethyl)-4(4-butylbenzyl)-undecanoic acid, dimeglumine salt, 0.005 molar of the Ca(II) complex of the 3,6,9-tris (carboxymethyl)-4-(4-butylbenzyl)-undecanoic acid, trimeglumine salt in 5% mannitol, pH 7.0.

The solution is infused over 30 minutes in a dosage of 0.3 mmol/kg of body weight. CT scannings are performed in the usual way before the beginning of the infusion, at the end of the infusion, and 30 minutes after the end of the infusion.

Example 4

3,6,9-Triaza-3,6,9-tris(carboxymethyl)-4-(4-ethoxybenzyl)-undecanoic acid disodium salt was complexed with different X-ray-absorbing metal ions and then the density values of the samples were measured in a water phantom at different concentrations, which corresponded in the dimensions to about the abdomen of a human. The operation was performed on a commercial computer tomograph at the usual voltage of 137 kV and 110 mA.

Findings in Houndsfield units (±SD)

TABLE 2

| Element | Concentration (mmol/L) | HU ± SD |
|---|---|---|
| $H_2O$ | — | 14 ± 23 |
| Gd | 50 | 218 ± 23 |
|  | 500 | 1680 ± 33 |
| Tb | 50 | 228 ± 25 |
|  | 500 | 1760 ± 45 |
| Dy | 50 | 226 ± 23 |
|  | 500 | 1840 ± 42 |
| Ho | 50 | 221 ± 29 |
|  | 500 | 1890 ± 40 |
| Er | 50 | 254 ± 24 |
|  | 500 | 1955 ± 57 |
| Yb | 50 | 252 ± 18 |
|  | 500 | 1980 ± 42 |
| I | 50 | 110 ± 25 |
|  | 500 | 914 ± 27 |

It turns out that there is a surprisingly high effectiveness of the rare earths relative to the iodine, which is presumably attributable to the special measuring conditions existing in the abdominal CT. Within the lanthanides, erbium, ytterbium and holmium are to be preferred to the previously most studied elements gadolinium and dysprosium.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of computer tomography of the liver and/or biliary tracts of a human patient, the improvement comprising:

administering to said patient a contrast-enhancing metal complex of a metal ion of atomic number 39–42, 44–51 or 56–83 and a complexing agent, wherein said metal complex is a compound of formula II

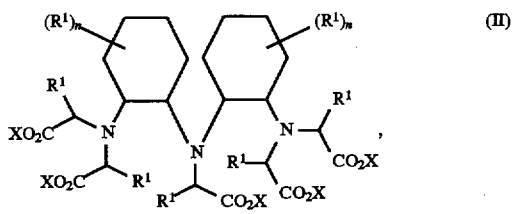

wherein

X is, in each case independently of one another, hydrogen or a metal ion equivalent of atomic number 39–42, 44–51 or 56–83,

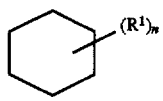

stands for a $C_6$-ring, which can be saturated, unsaturated or aromatic, and which is substituted n-fold by group $R^1$, n is 0, 1 or 2, and $R^1$ is, in each case independently of one another, hydrogen or a radical of formula IIa,

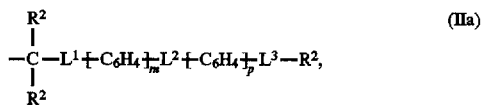

wherein m and p are each independently 0 or 1, $R^2$ is, in each case independently of one another, hydrogen or a branched or unbranched, saturated or unsaturated $C_1$-$C_6$ aliphatic radical, and $L^1$, $L^2$ and $L^3$ are each independently a direct bond, an oxygen atom, a sulfur atom, —N(H)—, —N($R^2$)— or a $C_1$-$C_{10}$-alkylene chain, optionally interrupted by an oxygen or a sulfur atom, an —N(H)— or an —N($R^2$)— group, wherein if m and/or p is equal to zero, no two or more heteroatoms are connected directly with one another;

wherein each free carboxyl groups not involved in complexing can also be present as a salt of a physiologically compatible cation or as an amide of formula

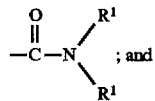

wherein said metal complex contains at least one radical of formula IIa.

2. A method according to claim 1, wherein said metal complex exhibits a stability constant of at least $10^{14}$ and a molecular weight of at most 1500 daltons.

3. A method according to claim 1, wherein said metal is a metal of the lanthanide series.

4. A method according to claim 3, wherein said metal is gadolinium, dysprosium, holmium, erbium, ytterbium or lutetium.

5. A method according to claim 1, wherein said metal is a metal of atomic number 72–83.

6. A method according to claim 5, wherein said metal is bismuth or lead.

7. A method according to claim 1, wherein said metal is a metal of atomic number 39–42.

8. A method according to claim 1, wherein said metal is a metal of atomic number 44–51.

9. A method according to claim 1, wherein said metal complex contains one or two radicals of formula IIa.

10. A method according to claim 1, wherein formula IIa stands for —$CH_2$-$C_6H_5$, —$CH_2$-$C_6H_4$—O—$CH_3$, —$CH_2$-$C_6H_4$—O—$CH_2CH_3$, —$CH_2$-$C_6H_4$—O—$C_3H_7$, —$CH_2$-$C_6H_4$—O—$C_4H_9$, —$CH_2$-$C_6H_4$—O—$C_5H_{11}$, —$CH_2$-$C_6H_4$—O—$CH_2$-$C_6H_5$, —$CH_2$-$C_6H_4$—$CH_3$, —$CH_2$-$C_6H_4$—$CH_2CH_3$, —$CH_2$-$C_6H_4$—$C_3H_7$, —$CH_2$-$C_6H_4$—$C_4H_9$, —$CH_2$-$C_6H_4$—$C_5H_{11}$ or —$CH_2$-$C_6H_4$—$CH_2$-$C_6H_5$.

11. A method according to claim 1, wherein said metal is lutetium.

12. A method according to claim 1, wherein said metal is ytterbium.

13. A method according to claim 1, wherein said metal complex is administered in an amount of 0.1–1.5 mmol/kg of body weight.

14. A method according to claim 1, wherein said metal complex is administered in an amount of 0.2–0.6 mmol/kg of body weight.

15. A method according to claim 1, wherein n is 1.

16. A method according to claim 1, wherein the density enhancement of healthy liver parenchyma is at least 10 Houndsfield units.

17. A method according to claim 1, wherein the density enhancement of healthy liver parenchyma is at least 17 Houndsfield units.

18. A method according to claim 1, wherein said metal is dysprosium.

19. In a method of computer tomography of the liver and/or biliary tracts of a human patient, the improvement comprising:

administering to said patient a contrast-enhancing metal complex of a metal ion of atomic number 39–42, 44–51 or 56–83 and a complexing agent, wherein said metal complex is a compound of formula III

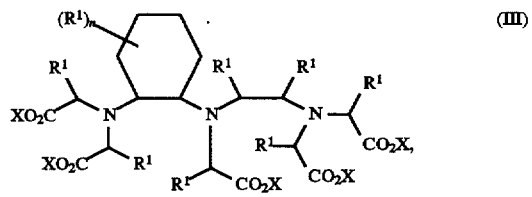

wherein

X is, in each case independently of one another, hydrogen or a metal ion equivalent of atomic number 39–42, 44–51 or 56–83,

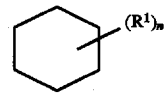

stands for a $C_6$-ring, which can be saturated, unsaturated or aromatic, and which is substituted n-fold by group $R^1$, n is 0, 1 or 2, and $R^1$ is, in each case, independently of one another, hydrogen or a radical of formula IIIa

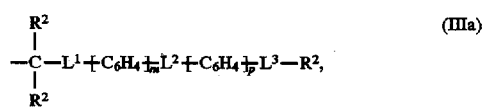

wherein m and p are each independently 0 or 1, $R^2$ is, in each case independently of one another, hydrogen or a branched or unbranched, saturated or unsaturated $C_1$-$C_6$ aliphatic radical, and $L^1$, $L^2$ and $L^3$ are each independently a direct bond, an oxygen atom, a sulfur atom, —N(H)—, —N($R^2$)— or a $C_1$-$C_{10}$-alkylene chain, optionally interrupted by an oxygen or a sulfur atom, an —N(H)— or an —N($R^2$)— group, wherein if m and/or p is equal to zero, no two or more heteroatoms are connected directly with one another, wherein each free carboxyl group not involved in complexing can also be present as a salt of a physiologically compatible cation or as an amide of formula

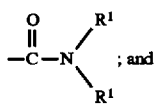

wherein said metal complex contains at least one radical of formula IIIa.

20. A method according to claim 19, wherein said metal complex contains one or two radicals of formula IIIa.

21. A method according to claim 19, wherein formula IIIa stands for $-CH_2-C_6H_5$, $-CH_2-C_6H_4-O-CH_3$, $-CH_2-C_6H_4-O-CH_2CH_3$, $-CH_2-C_6H_4-O-C_3H_7$, $-CH_2-C_6H_4-O-C_4H_9$, $-CH_2-C_6H_4-O-C_5H_{11}$, $-CH_2-C_6H_4-O-CH_2-C_6H_5$, $-CH_2-C_6H_4-CH_3$, $-CH_2-C_6H_4-CH_2CH_3$, $-CH_2-C_6H_4-C_3H_7$, $-CH_2-C_6H_4-C_4H_9$, $-CH_2-C_6H_4-C_5H_{11}$ or $-CH_2-C_6H_4-CH_2-C_6H_5$.

22. A method according to claim 19, wherein said metal is a metal of the lanthanide series.

23. A method according to claim 22, wherein said metal is gadolinium, dysprosium, holmium, erbium, ytterbium or lutetium.

24. A method according to claim 19, wherein said metal is a metal of atomic number 72–83.

25. A method according to claim 24, wherein said metal is bismuth or lead.

26. A method according to claim 19, wherein said metal is a metal of atomic number 39–42.

27. A method according to claim 19, wherein said metal is a metal of atomic number 44–51.

28. A method according to claim 19, wherein said metal is gadolinium, dysprosium, holmium, erbium, ytterbium or lutetium.

29. A method according to claim 19, wherein said metal is lutetium.

30. A method according to claim 19, wherein said metal complex is administered in an amount of 0.1–1.5 mmol/kg of body weight.

31. A method according to claim 19, wherein said metal complex is administered in an amount of 0.2–0.6 mmol/kg of body weight.

32. A method according to claim 19, wherein n is in each case 1.

33. A method according to claim 19, wherein the density enhancement of healthy liver parenchyma is at least 10 Houndsfield units.

34. A method according to claim 19, wherein the density enhancement of healthy liver parenchyma is at least 17 Houndsfield units.

35. A method according to claim 19, wherein said metal is dysprosium.

* * * * *